United States Patent [19]

Melville

[11] 3,952,331
[45] Apr. 27, 1976

[54] PROTECTIVE EYE SHADE FOR SPORTSMEN

[76] Inventor: Thomas Melville, 65-46 100th St., Flushing, N.Y. 11365

[22] Filed: Oct. 9, 1974

[21] Appl. No.: 513,326

[52] U.S. Cl. .................................. 2/14 H; 2/9
[51] Int. Cl.² .................................. A61F 9/00
[58] Field of Search ............... 2/14 H, 14 UT, 14 B, 2/14 T, 14 R, 9, 12, 15, 14 C, 14 D, 14 F, 14 J, 14 K, 14 Y; 351/111, 123

[56] References Cited
UNITED STATES PATENTS

| | | | |
|---|---|---|---|
| 1,336,009 | 4/1920 | Wilmer | 2/14 F |
| 1,523,521 | 1/1925 | Goodman | 2/9 |
| 2,920,327 | 1/1960 | Singer | 2/14 R |
| 3,006,247 | 10/1961 | Davis | 351/123 |
| 3,389,406 | 6/1968 | Mitchell | 2/14 R |

FOREIGN PATENTS OR APPLICATIONS 329,470  5/1930  United Kingdom .............. 2/14 B Primary Examiner—Thomas F. Callaghan
Assistant Examiner—Peter Nerbun
Attorney, Agent, or Firm—Charles E. Temko

[57] ABSTRACT

A protective eyeshade device particularly adapted to be used by golfers while on the fairway of a golf course as a protection against golf balls in flight. The device includes cushioning elements positioned in the area of the brow and temples, and a nose piece overlying the boned portion of the nose of the wearer. Cylindrically shaped lenses are formed of high impact synthetic resinous materials permitting flexing under the impact of a golf ball while transmitting the impact to the cushioning elements. The device is removed for actual playing of a game of golf, and the outer surfaces of the temple members are provided with pocket engaging clip means for this purpose.

3 Claims, 3 Drawing Figures

U.S. Patent  April 27, 1976  3,952,331
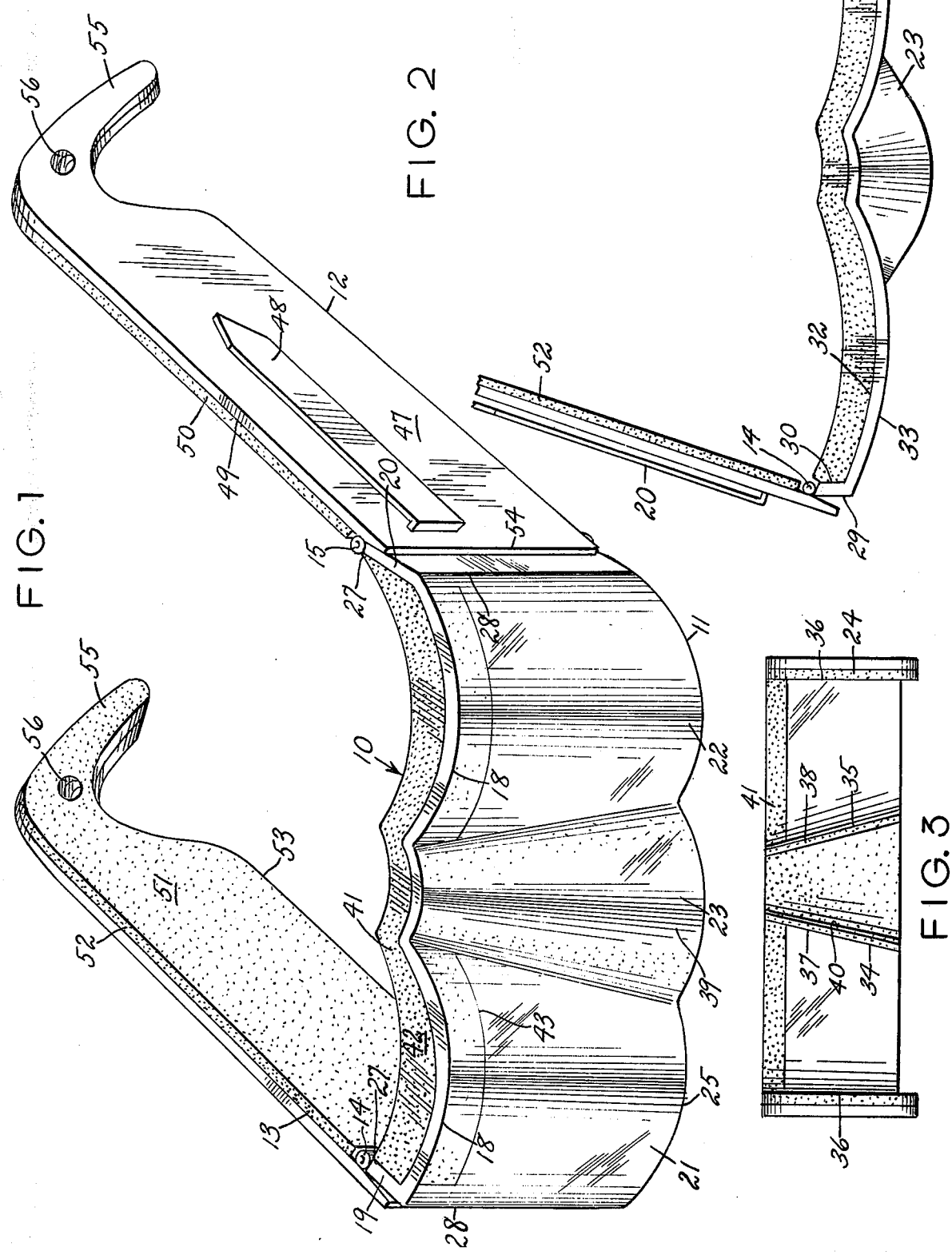

PROTECTIVE EYE SHADE FOR SPORTSMEN

BACKGROUND OF THE INVENTION

This invention relates generally to the field of protective devices for sportsmen, and more particularly to a protective eyeshade or shield suitable for use by golfers while on the fairway to protect them from stray balls of other golfers.

The use of cushioning elements in goggles to distribute the relatively heavy weight of such goggles is known in the art, as exemplified by the disclosure in U.S. Pat. No. 3,389,406. Such padding is under substantial compression while the goggles are worn, and as a consequence, such padding is relatively uncomfortable. U.S. Pat. No. 2,774,279 discloses a centrally disposed plastic nose engaging support in conjunction with conventional spectacles. It protects only the bridge of the nose, and not the length thereof.

SUMMARY OF THE INVENTION

Briefly stated, the invention contemplates the provision of a shade or shield of the class described adapted to overlie the portion of the face of a wearer to completely shield the eyes, nose and temples, and provide substantial shock absorbancy for the outer ears, thereby protecting the most vulnerable parts of the head of the wearer against the impact of a golf ball. This is accomplished by providing a first element of high impact synthetic resinous material having interval lenses and nose covering member, the upper margin of which is heavily padded, and which is under relatively little compression during the wearing of the device by virtue of the fact that it is supported by the upper surface of the nose of the wearer. Side temple elements are of a width substantially equal to the height of the first-mentioned element, and are padded on an inner surface thereof, the same being hingedly connected to the first-mentioned element. The padding on the temple elements is normally under relatively light compression in the absence of impact to provide frictional resistance to accidental displacement. Although the lense portions are transparant to permit the wearing of the device for extended periods, the device is easily demountable to prevent any possible optical distortion while the wearer is actually playing. Interval clip members are provided for convenient storage, which clip members are for added shock absorbancy while the device is worn.

FIG. 1 is a perspective view of the protective eyeshade device,

FIG. 2 is a top plan veiw and

FIG. 3 is a frontal inside view.

DETAILED DESCRIPTION OF THE DISCLOSED EMBODIMENT

In accordance with the invention, the device, generally indicated by reference character 10, comprises broadly: a front element 11, left and right temple elements 11 and 12, respectively, and hinge beams 14 and 15 interconnecting the elements 12 and 13 to the element 11.

The front element 11, as has been mentioned, is preferably molded integrally from high impact synthetic resinous materials. Plexiglass (Rohm and Hass, Philadelphia, Pennsylvania) is suitable, although rather expensive. Cellulose acetates are also suitable, where lower cost of manufacture is desired, as are other similar low cost synthetic resinous materials. The element is bounded by a continuous upper edge 18. Side flanges 19 and 20 extend rearwardly from corresponding eye cover or lenses 21 and 22, respectively. A hollow nose piece 23 interconnects the covers 21–22, and is provided with internal padding at 24 (see FIG. 3). A lower edge 25 is also continuous, the distance between the upper edge 18 and the lower edge 25 allowing the covers 21–22 to extend down to the lower edge of the nose of the wearer (not shown).

The side flanges 19 and 20 are similar and symmetrical, each being of planar configuration as best seen in FIGS. 1 and 2. Each is bounded by a rear edge 27, a forward edge 28 which partially overlies a respective side flange 19–20, as well as an outer surface 29 and an inner surface 30.

The covers or lenses 21–22 are of arcuate or cylindrical configuration, and provide an undistorted, uncorrected, view to the wearer. Each is bounded by an inner concave surface 32, an outer convex surface 33, and a pair of relatively centrally disposed vertical edges as at 34 and 35. The outer edges 36 merge with the side flanges 19–20.

The nose piece 23 includes a pair of side members 37, 38 interconnecting a central member number 39 which rests upon the upper surface of the nose of the wearer. A hollow recess 40 encloses the padding 24, as above-mentioned.

A recess 40 formed between the inner surfaces of the side flanges 19 and 20 is provided with a padding number 41, preferably of synthetic resinous foam, such as polyurethane or the like. An upper surface 42 is disposed in co-planar relation with respect to the edge 18. A lower edge 43 is positioned above the viewing areas of the covers 21–22 so that a rear surface 43 may rest in relatively uncompressed condition against the brow of the wearer.

The temple elements 13 and 14 are also formed from synthetic resinous material. Each is bounded by an outer surface 47 having integrally molded clip means 48 thereon, as well as an inner surface 49 provided with synthetic resinous foam padding 50 approximately ⅛ inch in thickness. The inner surface 51 of the padding contacts the temples of the wearer, thereby providing frictional retention of the device upon impact. An upper edge 52 is continuous with the edge 18 of the front element 11, and a lower edge 53 is continuous with the lower edge 25 of the element 11. A forward edge 54 extends past the hinge means 14–15 to conceal the same, and a rearwardly-extending hook portion 55 engages the ears of the wearer as with conventional spectacles. An optional through opening 56 in each element 12–13 allows the same to be supported in front of the wearer by a strap or string (not shown) in well-known manner.

While wearing the spectacles the device is supported principally by the hook portions 55 of the temple elements and the inner surface of the nose piece 23 resting upon the nose of the wearer. The padding 41 and 50 rest relatively lightly upon the brow and temples of the wearer, and being porous, can absorb limited amounts of perspiration. Upon the occurrence of impact on the covers 21–22 or the temple elements 12 and 13, the synthetic resinous parts will flex to absorb shock, and the padding disposed there beneath will compress to supplement this action. Unless the nose piece 23 is directly contacted, the remaining parts can flex relative to it for maximum shock absorbancy.

Because of the curvature of the eye covers 21–22 (best seen in FIG. 2) the nose piece 23 will normally not be struck outside of an angle of approximately 20 degrees to either side of a vertical plane passing through the nose piece. When this occurs, shock will be absorbed by the padding 24, as well as the padding 41. Impact on any other part of the device will normally be transmitted to the remaining parts of the device, so that a substantial part of the padding will contribute to shock absorbancy. Should impact be made upon the clip means 48, additional shock absorbancy is obtained.

I wish it to be understood that I do not consider the invention limited to the precise details of structure shown and set forth in this specification, for obvious modifications will occur to those skilled in the art to which the invention pertains.

I claim:

1. A protective eye and face shield for sportsmen comprising: a unitary transparent front element of high impact synthetic resinous material, said element including integrally molded first and second covers adapted to overlie the eyes of a wearer, and a nose piece interconnecting said covers and adapted to overlie at least a portion of the nose of said wearer, said nose piece being so contoured that the weight of said element is distributed along the length thereof when the device is worn; said front element being bounded by an upper edge lying in a horizontal plane, and a lower edge substantially parallel to said upper edge; and left and right planar temple elements pivotally interconnected substantially at forward edges thereof to side edges of said front element, said temple elements having a vertical height substantially equal to that of said frontal element; a padding member of generally elongated configuration secured to an upper edge portion of the inner surface of said front element, and extending between left and right temple elements, said padding member having an exposed rearward surface adapted to lightly contact the brow of a wearer; and planar padded members secured to the inner surfaces of said temple elements to cushion said temple elements relative to the sides of head of said wearer, said temple elements having rearwardly positioned means for engaging the ears of said wearer; whereby upon the occurrence of an impact from a golf ball or similar missile upon an exposed surface of said shield, said impact is absorbed by the flexing of said resinous material and compression of said padding member.

2. Structure in accordance with claim 1, further characterized in said temple elements having clip means on an outer surface thereof.

3. Structure in accordance with claim 1, further characterized in said nose piece having additional padding on an inner surface thereof.

* * * * *